United States Patent [19]

Alferness

[11] B 3,999,556

[45] Dec. 28, 1976

[54] DEMAND CARDIAC PACEMAKER WITH INPUT CIRCUIT PORTION OF INCREASED SENSITIVITY

[75] Inventor: Clifton Alferness, Minneapolis, Minn.

[73] Assignee: Medtronic, Inc., Minneapolis, Minn.

[22] Filed: Dec. 16, 1974

[21] Appl. No.: 533,259

[44] Published under the second Trial Voluntary Protest Program on February 24, 1976 as document No. B 533,259.

[52] U.S. Cl. .......................... 128/419 PG; 330/138
[51] Int. Cl.² .......................................... A61N 1/36
[58] Field of Search ........... 128/419 PG, 421, 422; 307/318, 302; 330/129, 138; 328/146, 148; 323/75 F, 222

[56] References Cited

UNITED STATES PATENTS

| | | | |
|---|---|---|---|
| 3,661,158 | 5/1972 | Berkovits | 128/419 PG |
| 3,768,486 | 10/1973 | Berkovits et al. | 128/419 PG |
| 3,832,703 | 8/1974 | Lenert | 307/318 |

Primary Examiner—William E. Kamm
Attorney, Agent, or Firm—Cameron, Kerkam, Sutton, Stowell & Stowell

[57] ABSTRACT

A demand cardiac pacemaker is disclosed as comprising an input sensing circuit portion of improved sensitivity to heart beat signals of relatively low amplitude. In particular, the input circuit portion includes a first sensing, bipolar transistor biased by a GaAsP light-emitting diode (LED), and a second amplifying, bipolar transistor whose base is coupled to the collector of the first transistor. Further, the output of the second transistor as taken from its collector is fed back through a suitable shaping circuit to the emitter of the first transistor, whereby controlled high gain and desired frequency/amplitude discrimination characteristics are achieved from the first and second transistors, so that the input sensing portion of the pacemaker circuit is responsive to heart signals above a predetermined level without sacrificing gain.

6 Claims, 7 Drawing Figures

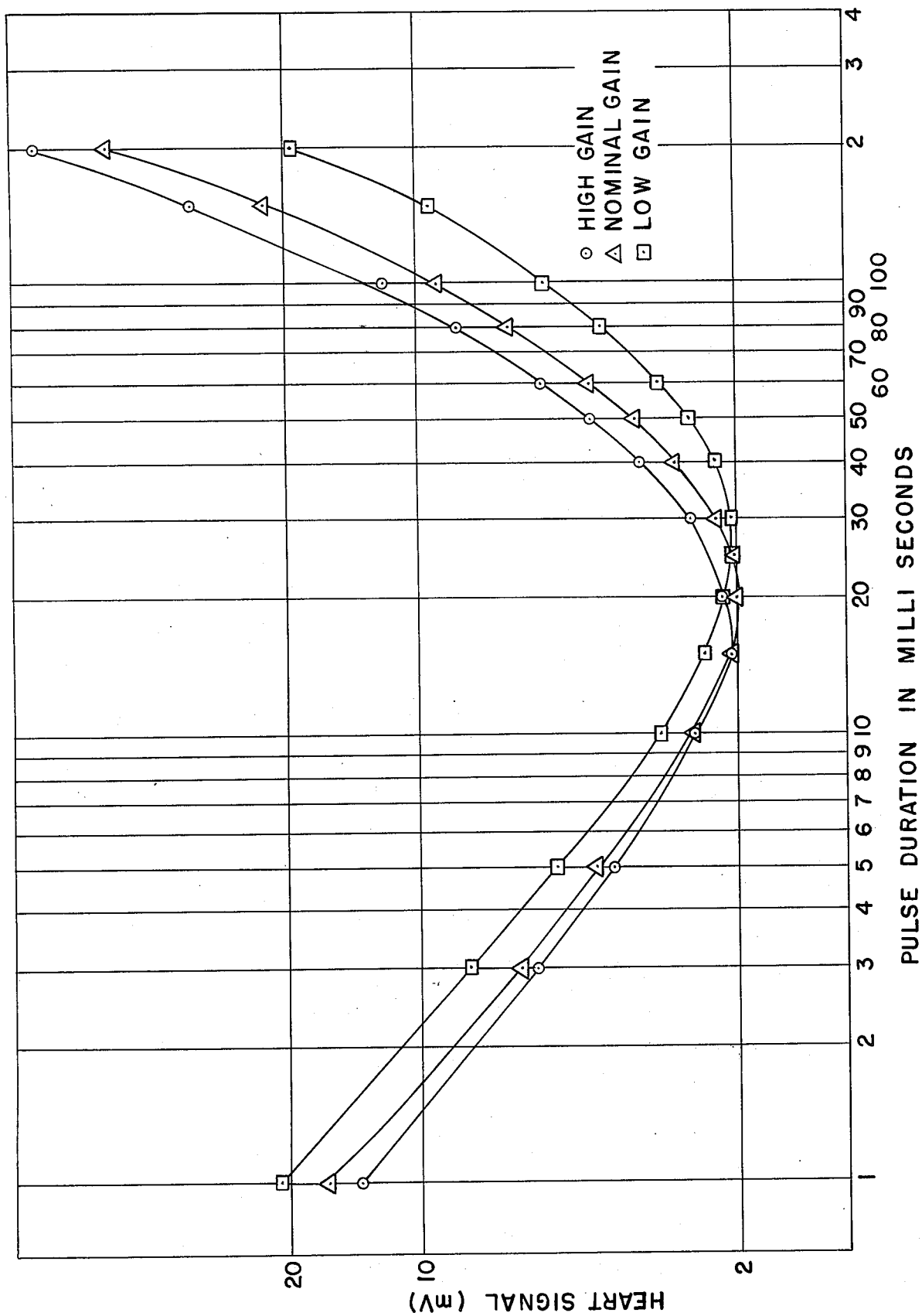

DEMAND CARDIAC PACEMAKER WITH INPUT CIRCUIT PORTION OF INCREASED SENSITIVITY

BACKGROUND OF THE INVENTION

1. Field of the Invention

This invention relates to electronic cardiac pacemakers implantable within the human body and more particularly to cardiac pacemakers which respond to a heart signal to inhibit the pacemaker output and in the absence of a heart signal, provide a regular stimulating signal to the patient's heart.

2. Description of the Prior Art

Heart pacers such as that described in U.S. Pat. No. 3,057,356 issued in the name of Wilson Greatbatch and assigned to the assignee of this invention, are known for providing electrical stimulus to the heart, whereby it is contracted at a desired rate in the order of 72 beats per minute. Such a heart pacemaker is capable of being implanted in the human body and operative in such an environment for relatively long periods of time. Typically, such pacemakers are implanted within the chest beneath the patient's skin and above the pectoral muscles or in the abdominal region by a surgical procedure wherein an incision is made in the selected region and the pacemaker is implanted within the patient's body. Such a pacemaker provides cardiac stimulation at low power levels by utilizing a small, completely implanted transistorized, battery-operated pacemaker connected via flexible electrode wires directly to the myocardium or heart muscle. The electrical stimulation provided by this pacemaker is provided at a fixed rate.

In an article by D. A. Nathan, S. Center, C. Y. Wu and W. Keller, "An Implantable Synchronous Pacemaker for the Long-Term Correction of Complete Heart Block," *American Journal of Cardiology*, 11:362, there is described an implantable cardiac pacemaker whose rate is dependent upon the rate of the heart's natural pacemaker and which operates to detect the heart beat signal as derived from the auricular sensor electrode and, after a suitable delay and amplification, delivers a corresponding stimulus to the myocardium and in particular, the ventricle to initiate each heart contraction.

Such cardiac pacemakers, separately or in combination, tend to alleviate some examples of complete heart block. In a heart block, the normal electrical interconnection in the heart between its atrium and its ventricle is interrupted whereby the normal command signals directed by the atrium to the ventricle are interrupted with the ventricle contracting and expanding at its own intrinsic rate in the order of 30–40 beats per minute. Since the ventricle serves to pump the greater portion of blood through the arterial system, such a low rate does not provide sufficient blood supply. In normal heart operation, there is a natural sequence between the atrial contraction and the ventricular contraction, one following the other. In heart block, there is an obstruction to the electrical signal due, perhaps, to a deterioration of the heart muscle or to scar tissue as a result of surgery, whereby a block in the nature of a high electrical impedance is imposed in the electrical flow from the atrium to the ventricle.

Where the heart block is not complete, the heart may periodically operate for a period of time thus competing for control with the stimulation provided by the artificial cardiac pacemaker. Potentially dangerous situations may arise when an electronic pacemaker stimulation falls into the "T" wave portion of each natural complete beat. As shown in FIG. 1, the "T" wave follows by about 0.2 seconds each major beat pulse (or "R" wave causing contraction of the ventricles of the heart). Within the "T" wave is a critical interval known as the "vulnerable period" and, in the case of a highly abnormal heart, a pacemaker impulse falling into this period can conveivably elicit bursts of tachylcardia or fibrillation, which are undesirable and may even lead to a fatal sequence of arythmias.

In U.S. Pat. No. Re. 28,003 of Wilson Greatbatch and assigned to the assignee of this invention, there is disclosed an implantable demand cardiac pacemaker comprising an oscillator circuit for generating a series of periodic pulses to be applied via a stimulator electrode to the ventricle of the heart. The stimulator electrode is also used to sense the "R" wave of the heart, as derived from its ventricle to be applied to a sensing portion of the cardiac pacemaker wherein, if the sensed signal is above a predetermined threshold level, a corresponding output is applied to an oscillator circuit to inhibit the generation of the stimulator pulse and to reset the oscillator to initiate timing a new period.

In FIG. 2, there is shown a portion of the heart pacemaker circuit as disclosed in U.S. Pat. No. Re. 28,003, wherein a suitable voltage source such as a battery, applies positive and negative potentials to buses 14 and 12, respectively. Further, the stimulator electrode is used to couple heart pulses via bus 10 and resistive element 18 to the gate of FET 28. As shown in FIG. 2, the FET 28 is suitably biased by resistive element 24. Further, oppositely disposed diodes 20 and 22 are coupled in-parallel with each other, to the gate of FET 28 to protect the FET from input voltages above and below predetermined levels. The output of FET 28 is applied to the base of transistor 36, suitably biased by resistive elements 30, 37 and 34. The output of the unipolar transistor 36 is in turn coupled by capacitor 38 to the remaining portion of the circuit as described and shown in detail in U.S. Pat. No. Re. 28,003.

As shown in FIG. 1, the human heart beat is a complex wave over the period of each beat and recognizably consists of "P," "Q," "R," "S" and "T" waves. The major and most pronounced pulse is the "R" wave and is normally of a magnitude between 2 and 10mV in the left ventricle, the "T" wave normally follows the "R" wave by approximately 0.2 seconds. The "R" wave typically has a pulse width in the order of 10 to 60msec and due to its relatively small amplitude, requires accurate detection and relatively high amplification to control the oscillator circuit of a demand pacemaker as described above. A significant problem in the use of an FET in such a sensing circuit is its relatively low gain, thus requiring the use of an open-loop type of amplification circuit to achieve the necessary high gain in the order of 300, for example. It is apparent that relatively high gains may be achieved by cascading a plurality of amplifying elements, but in the environment of a cardiac pacemaker, the size and therefore the number of elements that may be incorporated therein is limited. Further, it is difficult without the use of some type of negative feedback to achieve stable operation of the sensing and amplifying circuit and to avoid adjustment of the elements within this circuit to assure the desired frequency and amplitude discrimination. However, due to the limited gain of known FET's, it is difficult to achieve the necessarily high gain and at the same time use negative feedback, which limits the gain of the resulting amplification circuit. Further, it is difficult to bias accurately an FET when used to detect signals at relatively low current levels and further to achieve the desired frequency/amplification characteristics of the entire circuit to detect the heart pulses, without the use of feedback.

Further, it is desired in the design of a sensing portion of cardiac pacemaker circuits to ensure that the circuit as manufactured and adjusted at relatively low temperatures, e.g. a room temperature of 72°F, will detect accurately similar signals at elevated body temperatures, i.e., 98.6°F. In particular, the threshold level detection of the circuit set at the lower temperature may change as the temperature is raised due to differences in temperature coefficients of the biasing elements for the first detection element, an FET. Thus, if the biasing elements have a different temperature coefficient than that of the FET, the relative threshold level of the FET at an elevated temperature within the patient's body will change, thereby detecting signals of other frequencies/amplitudes than desired.

SUMMARY OF THE INVENTION

It is therefore an object of this invention to provide a new and improved demand heart pacemaker circuit with a sensing portion thereof of improved stability and amplitude/frequency discrimination characteristics.

It is a further object of this invention to provide an improved demand heart pacer circuit avoiding the defects of the prior art and in particular providing an improved method of biasing its input transistor.

These and other objects of the invention are accomplished by providing a heart demand pacemaker circuit with a sensing and amplifying portion thereof including a unidirectional conducting means for providing substantially constant biasing regardless of voltage source depletion, for a first bipolar, relatively high gain transistor. The output of the input bipolar transistor is applied to at least one further amplifying transistor, whose output is fed back to the first transistor through a filtering circuit to provide desired amplitude/frequency characteristics, whereby a heart signal and in particular the "R" wave, is sensed and if above a predetermined threshold level, is amplified, before being applied to inhibit an oscillator circuit of the pacemaker.

In a further feature of this invention, the unidirectional conducting means is of a type having a temperature coefficient substantially equal to that of the first bipolar transistor, whereby when the demand heart pacemaker circuit is implanted within a patient at an elevated temperature, the relative characteristics of the biasing element and the bipolar transistor remain the same and the bipolar transistor's threshold level is accurately maintained to sense only those heart signals above the predetermined threshold level.

DESCRIPTION OF THE DRAWINGS

FIG. 5 is a graph showing the amplitude output of the sensing and amplifying portion of the circuit of FIG. 3, as a function of the pulse duration in milliseconds of the signal applied thereto.

DESCRIPTION OF THE PREFERRED EMBODIMENT

Figure 1:
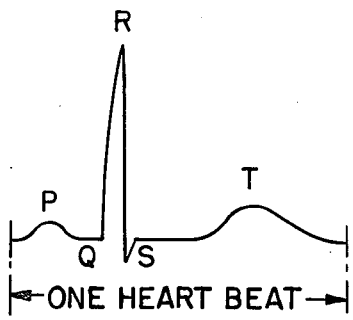
FIG. 1 illustrates the voltage wave produced by a human heart during one complete heart beat.
Figure 2:
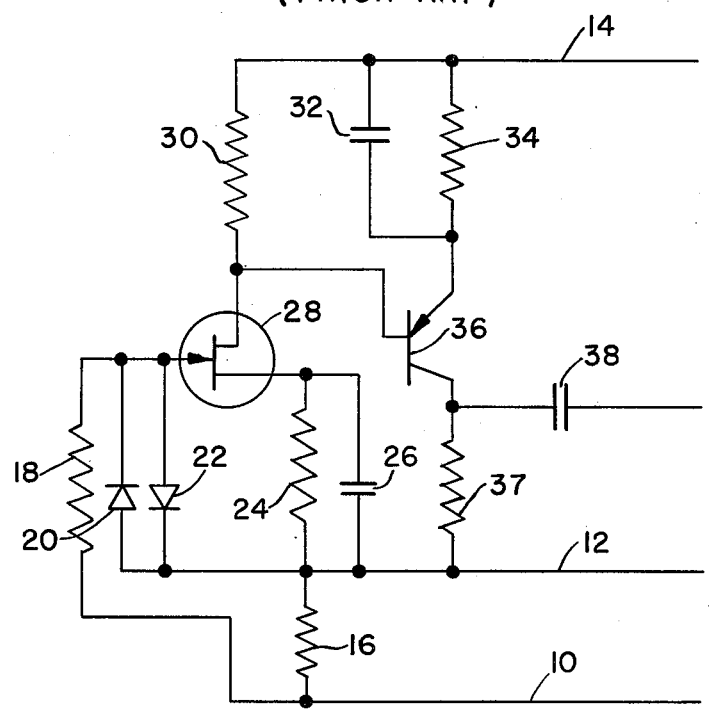
FIG. 2 is a schematic drawing above described of the sensing and amplifying portion of a demand heart pacemaker circuit of the prior art.
Figure 4A:
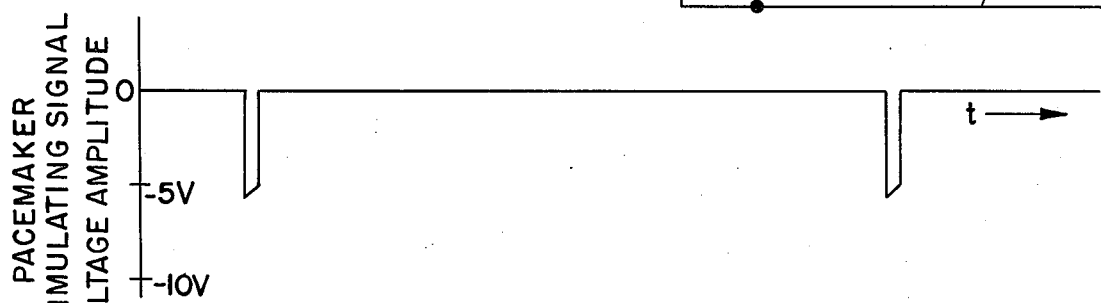
FIGS. 4A, 4B and 4C show various signals as applied to and developed by the circuit of FIG. 3.
Figure 4B:
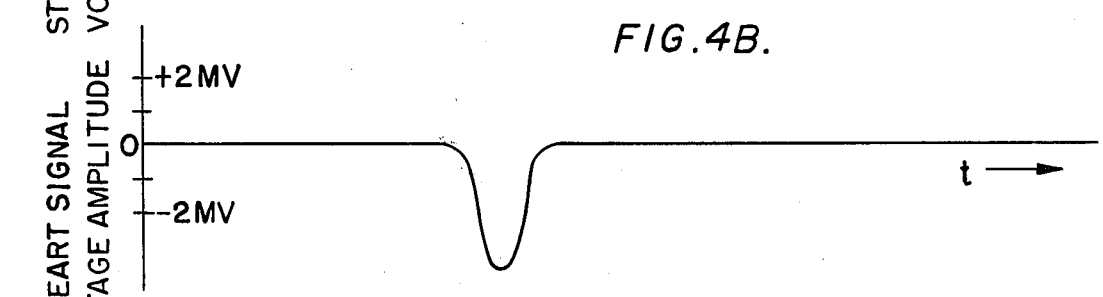
Figure 3:
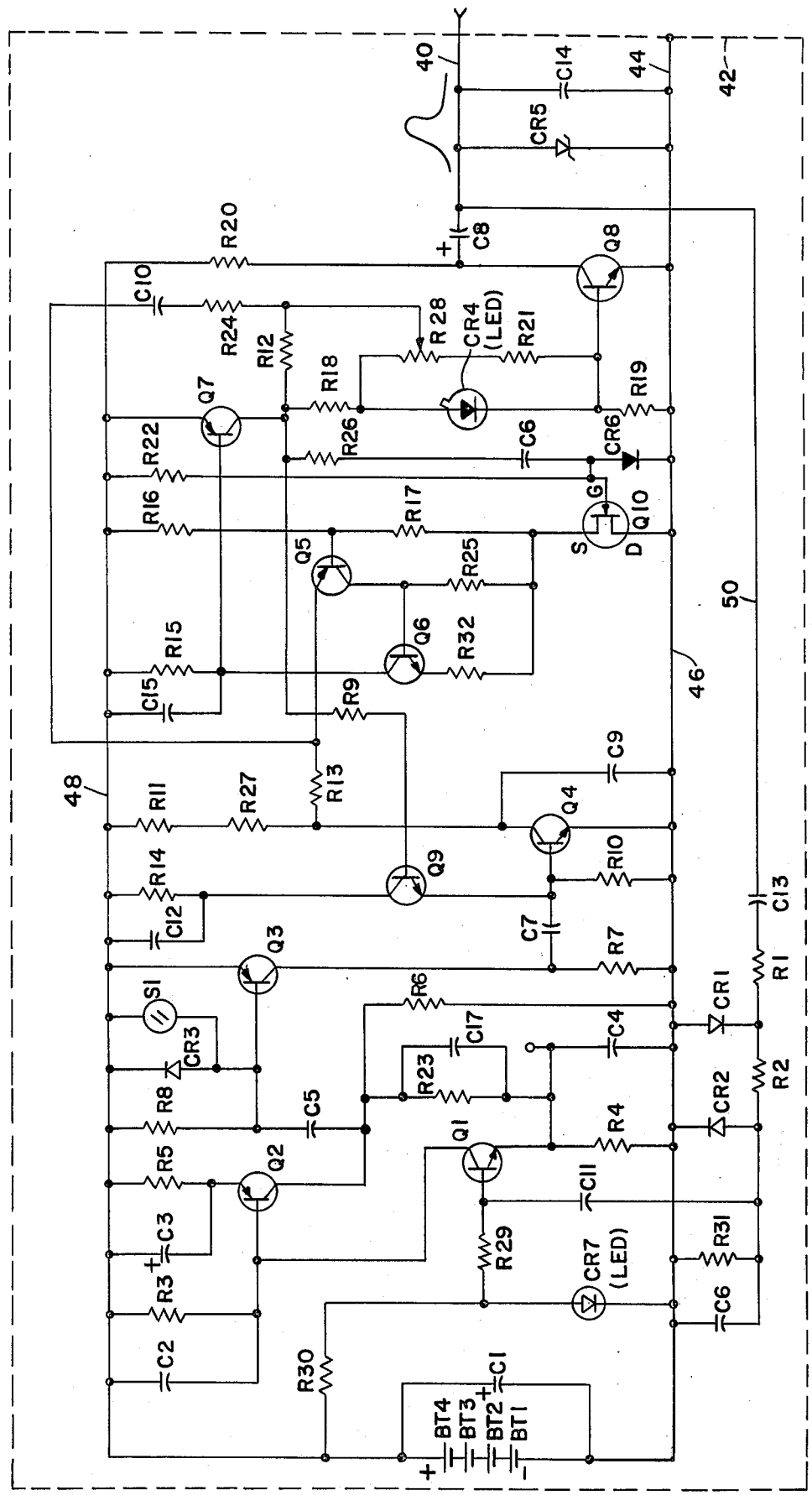
FIG. 3 is a schematic drawing of the complete circuit of an illustrative demand heart pacemaker, including the sensing and amplifying portion in accordance with the teachings of this invention.

The heart pacemaker as described herein is implanted into the patient by surgical procedure, typically into his chest region, to be disposed between the pectoralis muscle and the skin. As described above, a demand heart pacemaker circuit of the type herein is adapted to sense the "R" wave (shown in FIG. 1) as picked up by a stimulator electrode in place on or in the ventricle and electrically coupled to an input lead 40 as shown in FIG. 3. The circuit of FIG. 3 has a second, indifferent electrode which may take the form of a conductive metallic shield 42 disposed about the pacemaker circuit and coupled to a second input lead 44. As the name implies, the stimulator electrode is not only used to sense the natural "R" waves of the ventricular region of the heart, but also is used to apply stimulating pulses to the ventricle of the heart. The "R" wave as sensed by the stimulator electrode is applied by leads 40 and 50 to be shaped by a differentiating circuit formed of capacitor C13 and resistive elements R1, R2 and R31, before being coupled by capacitor C11 to the base of input bipolar transistor Q1. The input "R" wave signal is shown in FIG. 4B and has a waveform corresponding to a $\sin^2$ function and a duration in the order of 10 to 60msec. The amplitude of the "R" wave signal to be sensed varies from 2 to 10mV and it is desired to set the threshold of the sensing circuit (to be described) with high precision in the order of 2 to 4mV. The sensing circuit is characterized by not only an amplitude, but a frequency discrimination, whereby extraneous signals of differing pulse widths and amplitudes are discriminated against. The pacemaker circuit and in particular its indifferent electrode formed by the shield 42, is disposed in direct contact with the pectoralis muscle, whereby myoelectric or motor muscle signals are readily imposed thereon and must be discriminated against with respect to the "R" wave signals as derived from the ventricle. To this end, the myoelectric signals are typically lower in amplitude, e.g. lower than 2mV, and by accurately establishing the threshold voltage level with which the input transistor Q1 is biased on, these signals may be effectively discriminated against.

In FIG. 3, a voltage source comprised of batteries BT1, BT2, BT3 and BT4 serve to energize the pacemaker circuit, applying a positive potential to a bus 48 and a negative potential to a bus 46. Further, a pair of diodes CR1 and CR2 are oppositely connected between lead 50 and bus 46, whereby signals of an amplitude greater than that of the signals of interest are limited to protect the pacemaker circuit. The input signal is applied by the capacitor C11 to the base of transistor Q1 which is a bipolar, NPN transistor having a relatively large gain, and in particular a significantly larger gain than the FET's of the prior art. In order to precisely bias the base of transistor Q1 and in a manner that is independent of the eventual depletion of the batteries BT1 to BT4, the base of transistor Q1 is connected to the mid-point between a unidirectional conducting device CR7 and a resistor R30, which circuit is connected in-parallel across the serially-connected batteries BT1 to BT4.

The unidirectional conducting device CR7 takes the form of a GaAsP light-emitting diode (LED), which accurately maintains a biasing voltage in the order of 1.3V (for example) upon its anode electrode, as applied through the resistor R29 to the base of transistor Q1. Such a unidirectional conducting device was chosen in preference to others, a zener diode, for example, due to its relatively sharp voltage/current characteristics and for its temperature coefficient characteristic, which closely resembles the base-to-emitter characteristics of the transistor Q1. The temperature coefficient of the LED CR7 is significant in that the process of manufacturing and testing the pacemaker circuit as shown in FIG. 3 is carried out at nominally room temperature, e.g. 72°F. As a part of the manufacturing procedure, the threshold voltage of transistor Q1 is tested to ensure that it does discriminate against signals below a predetermined level, e.g. 2mV, corresponding to myoelectric signals. However, the operating environment of the pacemaker circuit is within the human body at a normal temperature of 98.6°F. At these elevated temperatures, it is necessary to ensure that the voltage characteristics of the LED CR7 and transistor Q1 have changed a like amount, whereby the threshold level at which the transistor Q1 is turned on, remains the same, e.g. 2mV. In one illustrative embodiment, the LED CR7 as described above has a forward voltage temperature coefficient of approximately -2.2mV/C° which matches closely and is substantially coextensive with the base-to-emitter voltage temperature coefficient of the transistor Q1. As a result, the implanted circuit as shown in FIG. 3 does maintain its threshold level at which it detects heart signals with significant precision, even as its temperature is increased.

The demand pacemaker circuit as shown in FIG. 3 comprises at least three identifiable portions, comprising an input sensing and amplification portion comprising the input transistor Q1, responsive to the heart input signal for providing an output from a transistor Q4 which serves to inhibit the oscillator circuit generally shown on the right-hand portion of FIG. 3. The oscillator circuit output is derived from output transistor Q8 to apply a pulse of defined width and repetition rate to the stimulator electrode via lead 40. The stimulating pulse output as shown in FIG. 4A, has an output of 5 to 5.5V and a pulse width in the order of 0.5msec and is supplied to the stimulator electrode at a rate nominally of 72 beats per minute, i.e., a period of approximately 933msec. Further, in order to prevent the generation of a stimulating pulse at a time corresponding to the "T" wave portion, a refractory period after the generation of the pulse is provided in which the circuit and in particular the sensing and amplifying portion thereof is inhibited from providing an output.

As described above, the input sensing and amplification portion of the circuit of FIG. 3 includes the bipolar transistor Q1 for initially detecting and amplifying those signals above the predetermined threshold and upon being turned on, applying a signal from its collector to the base of transistor Q2. As seen in FIG. 3, the base and emitter of transistor Q2 are biased by the parallel combination of resistor R3 and capacitor C2, and the combination of resistor R5 and capacitor C3, respectively. Further, the output of transistor Q2 as derived from its collector is applied by coupling capacitor C5 to the base of a non-linear amplifying transistor Q3 and also via a feedback circuit comprised of the parallel combination of resistor R23 and capacitor C17 to the emitter of transistor Q1. Transistor Q2 provides a relatively high gain sufficient to permit the incorporation of the feedback circuit to the first-mentioned transistor Q1. The feedback circuit functions to filter the feedback signal and also to establish an overall amplitude/frequency discrimination characteristic of the input sensing and amplifying portion of the pacemaker circuit. In FIG. 5, there is shown the effect of such an amplifying and sensing circuit for various gains imparted to the input signal of a $sine^2$ waveform similar to that of the "R" wave and as a function of the pulse duration of the input signal. From FIG. 5, it can be seen that for the pulse widths of an "R" wave of interest, i.e., from 10 to 60msec, that a relatively high amplitude output signal is derived from transistor Q4, whereby signals of a significantly greater or less pulse duration are frequency discriminated against and only the signals of interest are effectively detected and amplified. This frequency discrimination characteristic is attributable to providing transistors Q1 and Q2 of relatively high gain with the feedback circuit comprising resistor R23 and capacitor C17.

The output as derived from the collector of transistor Q2 serves to alter the charge on capacitor C5 dependent upon the amplitude of the input signal applied to the transistor Q1. Capacitor C5 is connected in series with resistors R6 and R8 between buses 48 and 46 and is normally charged to a preset value. When transistor Q2 is rendered more or less conductive by the greater conduction or lower conduction of bipolar transistor Q1, the voltage on capacitor C5 changes accordingly. Thus, if the sensed amplitude of the heart signal is above the preset level, the charge on capacitor C5 is altered to a voltage sufficient to turn normally non-conducting transistor Q3 on. As a result, further amplitude discrimination is achieved whereby the detection of only "R" wave signals is insured.

The sensing and amplifying circuit of FIG. 3 is responsive to positive and negative heart signals. In particular, if a heart signal of a polarity is present to produce a negative potential upon the collector of transistor Q2, a current will be drawn through the emitter-to-base path of transistor Q3 and capacitor C5, whereby transistor Q3 is turned on. On the other hand, if a heart signal of an opposite polarity is placed upon the input of the sensing and amplifying circuit, a positive potential appears upon the collector of transistor Q2, thereby tending to turn transistor Q3 off and discharging capacitor C5 through diode CR3. However, when the positive potential is removed from the collector of transistor Q2, capacitor C5 charges through the base of transistor Q3, whereby transistor Q3 is turned on at that time. Further, a magnetically-actuated switch S1 is connected between the base of transistor Q3 and the positive bus 48, and serves to disable the sensing and amplifying circuit when the switch S1 is magnetically actuated. The switch S1 is inserted into the circuit to permit the doctor to disable the sensing and amplifying circuit by actuating the switch S1 with a suitable magnetic field and thereby render transistor Q3 non-conductive. With the sensing and amplifying circuit defeated, the generator circuit will freely oscillate and produce alternating signals at a rate dependent upon the battery voltage. Thus, the doctor may determine the operability of the pulse generator and the state of its batteries by monitoring the free-running rate and comparing the presently-measured rate to the rate exhibited at the time of implant.

In turn, the collector of transistor Q3 is coupled by capacitor C7 to the base of transistor Q4, which, when rendered conductive, in turn serves to inhibit the operation of the oscillator circuit in a manner to be described. Thus, the input detecting and sensing portion of the pacemaker circuit operates to sense those input signals corresponding to the "R" wave signals having an amplitude in excess of 2mV and a pulse width in the range of 10 to 60msec to turn on transistor Q4 and inhibit the oscillator circuit.

The portion of the circuit of FIG. 3 that provides a refractory period, that is a period following the production of a stimulating signal during which the sensing circuit is disabled to prevent sensing either the stimulating signal or the "R" wave signal responsive thereto, comprises the resistor R4 and the capacitor C4 connected in-parallel with each other, which combination is connected between the emitter of transistor Q1 and the bus 44. Upon the application of an input signal of sufficient amplitude to forward biased diode CR2 to the base of transistor Q1, transistor Q1 is rendered more conductive, and the capacitor C4, in emitter follower fashion, charges to a level corresponding to its quiescent voltage plus the forward biasing voltage of diode CR2, e.g. 0.4V. For the duration of the refractory period in the order of 300msec, transistor Q1 will not be turned on due to the additional positive charge placed upon its emitter by the voltage level to which capacitor C4 has been charged. Upon the removal of the input signal, capacitor C4 tends to discharge through resistor R4 to its normal biased quiescent potential, at which point the potential applied to the emitter of transistor Q1 is reduced, permitting transistor Q1 to be turned on. Thus, it can be seen that the values of capacitor C4 and resistor R4 are selected to provide a timing period corresponding to the desired refractory period.

The oscillating circuit now to be described with respect to FIG. 3 provides a stimulating pulse via the lead 40 to the stimulator electrode coupled to the ventricle of the patient's heart. The rate at which the pulse is applied to the heart is determined by a circuit comprising series-connected capacitor C9 and resistors R27 and R11 interconnected between the buses 48 and 46. As seen in FIG. 3, the capacitor is connected from the collector to the emitter of transistor Q4, which operates upon being turned on in response to the sensing and amplification of a heart pulse, to discharge capacitor C9, thereby terminating the timing period and resetting it to initiate timing a new, second period at point t2 in FIG. 4C, for example.

Figure 4C:
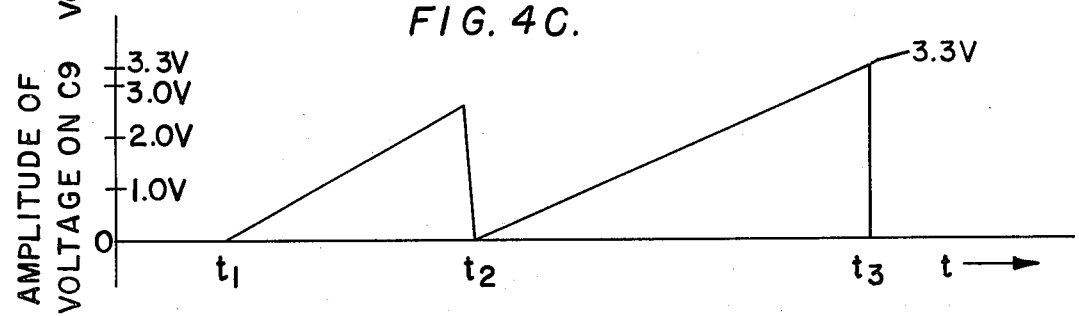

In the absence of detecting a heart signal, the capacitor C9 is charged by current flow through resistors R11 and R27 in a substantially linear manner as shown by the ramp-shaped signal in FIG. 4C. The voltage to which capacitor C9 charges is applied by resistor R13 to the emitter of transistor Q5. A reference voltage developed at the junction of resistors R16 and R17 is applied to the base of transistor Q5. When capacitor C9 has charged to its predetermined level, e.g. 3.3V, exceeding the reference voltage, transistor Q5 is turned on, thereby tending to raise the potential applied to the base of transistor Q6 toward the positive level established upon bus 48, whereby transistor Q6 is turned on. In turn, the collector voltage of transistor Q6 is applied to the base of transistor Q7 and as transistor Q6 is turned on, the potential applied to the base of transistor Q7 is lowered, whereby it is likewise turned on. As seen in FIG. 3, the collector of transistor Q7 is coupled via resistor R18 and the light-emitting diode (LED) CR4 to the base of the output transistor Q8. In particular, as transistor Q7 is turned on, it raises the potential applied to the base of transistor Q8 whereby it is turned on. Further, as transistor Q7 is turned on, a more positive potential is applied through resistor R9 to the base of transistor Q9, thereby tending to render it more conductive, whereby a more positive potential is likewise applied as by resistor R14 and transistor Q9 to the base of transistor Q4. As a result, transistor Q4 is rendered conductive, thereby discharging capacitor C9 from a potential of approximately 3.3V to 0V, as shown in FIG. 4C.

The pulse width of the stimulating pulses is determined by the period for which transistor Q8 is turned on and is set by the values of the elements of a second timing circuit comprising resistor R24 and capacitor C10. The second timimg circuit is coupled to the collector of transistor Q7 by resistor R12 and further is coupled back, as seen in FIG. 3, to the emitter of transistor Q5. The voltage with which the timing capacitor C10 is charged is determined by the setting of the potentiometer R28, which is connected in-series with resistor R21 across the LED CR4. Thus, the potential applied across the series-connected potentiometer R28 and resistor R21 is maintained relatively constant in spite of battery source depletion. Further, the tap of potentiometer R28 may be variably set to determine the charging current of capacitor C10 and therefore the pulse width of the stimulator pulse. Thus, as the transistor Q7 is rendered conductive, the voltage at the tap of resistor R28 is raised and the charging of capacitor C10 commences, whereby an increasing positive potential is applied to the emitter of transistor Q5 via lead 52 whereby after a period of time corresponding to the pulse width of the stimulator pulse, e.g. 0.5msec, the transistor Q5 is turned off. As a result, transistors Q6, Q7 and Q8 are likewise turned off, thereby terminating the stimulator pulse. Further, capacitor C10 is discharged when transistor Q4 is rendered conductive upon either sensing a heart signal above the predetermined amplitude or when transistor Q9 is rendered conductive, whereby a conductive path is provided through resistors R13 and transistor Q4 to the negative bus 46. Thus, capacitor C10 is prepared for the next cycle of the oscillator to be charged and to time the pulse width of the heart stimulating signal. Further, as transistor Q7 is turned off or rendered non-conductive, a more negative potential is applied to the base of transistor Q9, thereby rendering it non-conductive. As a result, a more negative potential is applied via resistor R14 and transistor Q9 to the base of transistor Q4 rendering it non-conductive and permitting capacitor C9 to charge through resistors R27 and R11 toward the potential established upon bus 48, to commence the next timing cycle as indicated at time t3 in FIG. 4C.

In FIG. 3, the oscillator circuit includes an FET Q10 whose source is connected to the base of transistor Q5 and whose drain is connected to the negative bus 46. The gate of FET Q10 is connected through resistive element R22 to the positive bus 48 and also to the point of interconnection between the diode CR6 and the capacitor C6. In turn, the diode CR6 is further connected to the negative bus 46 whereas the capacitor C6 is connected in-series through resistive element R26 with the collector of transistor Q7. The FET Q10 serves to prevent the oscillator circuit from stimulating the patient's heart at too fast a rate in the event one of its elements should become defective in any manner. For example, if the resistance R16 becomes an open circuit, the transistor Q5 would turn on prematurely with the result that a very rapid, possibly dangerous series of stimulating pulses would be applied to the patient's heart. In operation, FET Q10 is normally biased to a conducting state. To terminate the pulse width of the stimulating heart pulse, transistor Q5 is rendered non-conductive in a manner as explained above, whereby transistors Q6 and Q7 are also rendered non-conductive. While transistors Q5, Q6 and Q7 are rendered conductive, capacitor C6 connected to the gate of FET Q10 is charged. When transistor Q7 is turned off, the negative charge established upon capacitor C6 serves to bias off FET Q10, thereby preventing FET Q10 from being turned on again for a period dependent upon the discharge time of capacitor C6. As shown in FIG. 3, capacitor C6 discharges primarily through resistive element R22 but also through resistive elements R18, R26, R19, R21 and R28, the discharge time being in the order of 500 to 600msec. While FET Q10 is rendered non-conductive, transistor Q5 and therefore transistors Q6, Q7 and Q8, may not be turned on. Thus, if one of the elements within the oscillator circuit becomes defective, thereby tending to turn transistor Q5 on prematurely, FET Q10 serves a protective function, preventing the premature conduction of the noted transistors and therefore limits the rate at which stimulating pulses may be applied to the patient's heart, to a rate in the order of 110 beats per minute.

In summary, the pacemaker circuit of FIG. 3 will continue to oscillate at a rate determined by the values of capacitor C9 and resistors R11 and R27 to produce a pulse of a width determined by the values of resistors R18, R12 and R24, and capacitor C10, until an inhibiting pulse is applied to the base of transistor Q4, whereby it is rendered conductive, and capacitor C9 is discharged to terminate the operation of the pulse generating circuit.

The stimulating signal applied to the patient's heart by the pacemaker lead 40 is developed by the discharge of the capacitor C8 during the conducting period of the transistor Q8 through a series path including transistor Q8, lead line 44, the electrodes of the pacemaker and the patient's body, lead line 40, and capacitor C8. During the interval between stimulating signals, capacitor C8 recharges to battery potential through bus 48, load resistor R20, capacitor C8, the pacemaker electrodes and the patient's body, and bus 46. The amplitude of the recharging signal is insufficient to trigger a contraction of the patient's heart muscle.

Thus, there has been shown a demand cardiac pacemaker circuit having an improved input sensing and amplification section particularly capable of frequency and amplitude distrimination upon input signals to distinguish the desired "R" wave signals to be detected and amplified from other signals such as myoelectric signals and for providing an output indicative of the "R" wave signals to inhibit the oscillator circuit. In addition, the temperature characteristics of the elements chosen to sense the input signal are substantially similar so that when the pacemaker circuit is implanted within the patient and its temperature raised, its preset amplitude threshold level is maintained.

What is claimed is:
1. A demand cardiac pacemaker circuit comprising:
 a. pulse generator means including timing circuit means operable for generating and applying output stimulator pulses at a selected frequency to the heart of the patient in which said demand pacemaker circuit is implanted; and
 b. sensing circuit means responsive to a heart signal not always above a predetermined amplitude and comprising a first bipolar transistor of relatively high gain, unidirectional conducting means coupled to its base for maintaining the bias level of the base of said transistor, said unidirectional conducting means comprising a semiconductor device having a junction whose temperature dependent coefficients are coextensive with those of said first bipolar transistor, input means for applying the heart signal to said base of said first transistor, a second bipolar transistor of relatively high gain for further amplifying the output of said first transistor, and a feedback circuit including filter circuit means for applying the output of said second transistor to said first transistor, said filter circuit means for shaping the feedback signal to provide desired amplitude/frequency response characteristics of said sensing circuit means, whereby said sensing circuit is responsive to input signals of an amplitude above a predetermined level for generating and applying inhibit signals to said pulse generator means.

2. The demand pacemaker circuit as claimed in claim 1, wherein said unidirectional conducting means comprises a light-emitting diode.

3. The demand pacemaker circuit as claimed in claim 2, wherein there is included a voltage supply source and said light-emitting diode is connected in-series with a resistive element thereacross, and the point of interconnection between said light-emitter diode and said resistive element is coupled to said base of said first bipolar transistor.

4. The demand heart pacer circuit as claimed in claim 1, wherein said unidirectional conducting means comprises a GaAsP light-emitting diode.

5. The demand pacemaker circuit as claimed in claim 1, wherein said filter circuit means comprises a resistive element and a capacitor element connected inparallel with each other, said capacitive element and said resistive element being of such values to establish the frequency discrimination characteristics of said inhibit circuit to attenuate against signals other than within a predetermined pulse width range.

6. The demand pacemaker circuit as claimed in claim 5, wherein the range is from 10 to 60msec.

* * * * *